United States Patent [19]

Elliott

[11] Patent Number: 4,813,930
[45] Date of Patent: Mar. 21, 1989

[54] ANGIOPLASTY GUIDING CATHETERS AND METHODS FOR PERFORMING ANGIOPLASTY

[75] Inventor: Clyde D. Elliott, Mountain Brook, Ala.

[73] Assignee: Dimed, Inc., Birmingham, Ala.

[21] Appl. No.: 107,942

[22] Filed: Oct. 13, 1987

[51] Int. Cl.⁴ .............................................. A61M 5/18
[52] U.S. Cl. ...................................... 604/53; 128/772; 604/108; 604/164; 604/96
[58] Field of Search ...................... 604/53, 95, 96, 106, 604/107, 108, 164, 265, 280; 128/772

[56] References Cited

U.S. PATENT DOCUMENTS 4,586,923  5/1986  Gould et al. .......................... 604/95

*Primary Examiner*—Allen M. Ostrager
*Attorney, Agent, or Firm*—John P. White; Peter A. Luccarelli

[57] ABSTRACT

The invention relates to an angioplasty guiding catheter and methods for performing coronary angioplasty on a patient, to dilate constrictions in blood vessels. The guiding catheter has an elongated first member having at least one lumen therethrough and a tip, at least one leg member, coupled to the first member, radially extendable from a retracted position generally in contact with the first member to an extended position generally away from the first member, for abutment against an internal wall of patient's cardiovascular system, and means for extending the leg member from the retracted position to the extended position, coupled to the leg member. The angioplasty methods of the present invention involves entering the patient's cardiovascular system, pericutaneously patient's cardiovascular system to a desired translating through the location proximate a constriction in a blood vessel, abutting against an internal wall of the cardiovascular system, advancing towards the constriction in a direction generally opposite the abutting, for overcoming resistance by the constriction to the advancing and dilating the vessel at the constriction site.

20 Claims, 1 Drawing Sheet

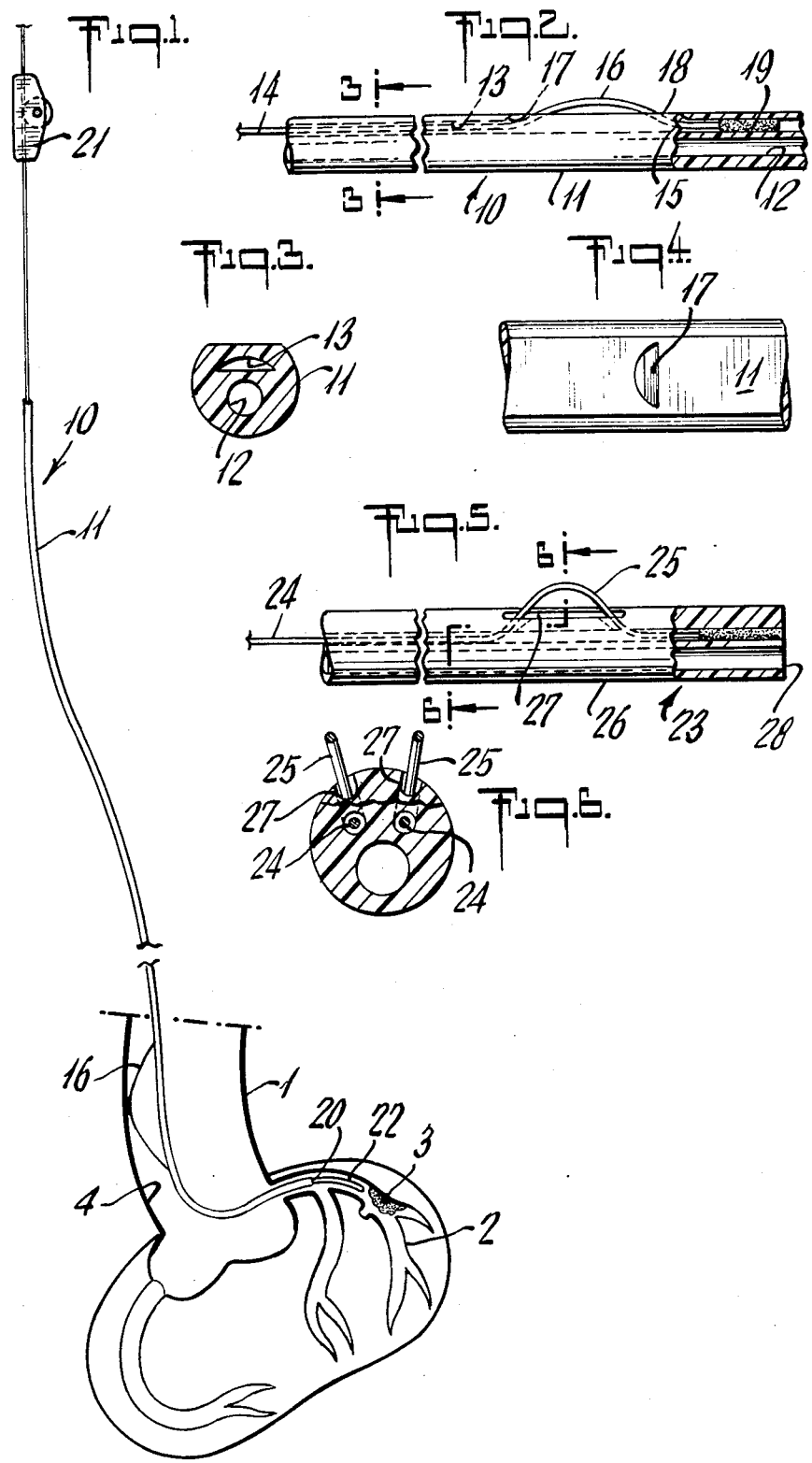

ANGIOPLASTY GUIDING CATHETERS AND METHODS FOR PERFORMING ANGIOPLASTY

BACKGROUND OF THE INVENTION

This invention relates generally to angioplasty and particularly angioplasty guiding catheters and methods for performing angioplasty on patients.

Coronary angioplasty procedures are known to cardiologists and they involve generally translating a guide wire and balloon catheter through a guiding catheter that has been routed through a patient's cardiovascular system, and positioning the balloon proximate a constricted portion of a blood vessel. Hydraulic pressure is then applied through the balloon catheter to bias against the vessel constriction, resulting in stretching and tearing of the constriction in the blood vessel, thus enlarging the vessel lumen and allowing more blood flow distal the constriction.

In order to deliver or direct a balloon catheter assembly into a blood vessel, the guiding catheter is made of stiffer material than is needed to seat itself in the ostium of the blood vessels. Guiding catheters are known to cardiologists and are constructed in an assortment of different configurations to fit various vessels, such as coronary arteries, bypass grafts and internal mammary arteries It is also known to cardiologists that guiding catheters serve two functions, namely they serve as delivery conduits for the wire and balloon angioplasty catheter assemblies, which angioplasty assemblies are of relatively delicate construction, and after an angioplasty catheter assembly is positioned proximate a constriction, the guiding catheter also provides support or pushing power to enable the physician to advance the deflated balloon assembly into and through the blood vessel constriction, so that biasing pressure can be efficiently applied and the vessel lesion can be dilated to a wider diameter.

Known angioplasty guiding catheters that are sold are constructed of layers of polymer material enclosing a wire braided support layer, which makes the catheter stiffer than one constructed solely of polymer material However, such wire supported polymer catheters do not have sufficient stiffness to overcome severe or rigid coronary obstructions or complicated, twisting curved sections of blood vessels. When such rigid obstructions or tortuous vessel curves are encountered, the guiding catheter tends to back away from the obstruction as the balloon catheter is advanced out of the guiding catheter and towards the lesion. Such lack of sufficient rigidity and stiffness in known catheters inhibits the treating physician from applying sufficient force with the guiding catheter, to allow passage of the balloon catheter across the lesion, thus rendering some lesions or other constrictions untreatable by the angioplasty technique It is an object of the present invention to develop a guiding catheter and method for performing angioplasty, that allows greater biasing leverage for advancing balloon catheters through tortuous vessels or severe constrictions than those guiding catheters and methods for performing angioplasty previously known in that art.

It is another object of the present invention to create a guiding catheter and methods for performing angioplasty, that allows the guiding catheter to pass through twisted, tortuous sections of a patient's cardiovascular system, yet provides sufficient rigidity to prevent backing away from vessel lesion sites.

It is also an object of the present invention to develop a guiding catheter having a wide assortment of construction configurations to fit various vessels, including coronary arteries, bypass grafts and internal mammary arteries.

SUMMARY OF THE INVENTION

These objects have been attained with the guiding catheter and method for performing angioplasty as described and claimed in the present invention. The guiding catheters described in the claims herein are especially suitable for performing angioplasty and may be configured in any previously known shape and structure, to fit various cardiovascular vessels, such as coronary arteries, bypass grafts and internal mammary arteries.

The angioplasty guiding catheter of the present invention comprises an elongated first member having at least one lumen therethrough and a tip; at least one leg member, coupled to the first member, radially extendable from a retracted position generally in contact with the first member to an extended position generally away from the first member, for abutment against an internal wall of a patient's cardiovascular system; and means for extending the leg member from the retracted position to the extended position; the extending means is coupled to the leg member.

The angioplasty guiding catheter of the present invention also comprises an elongated first member having first and second luma and a tip; at least one leg member, radially extendable from a retracted position generally in contact with the first member to an extended position generally away from the first member, having a resilient, elongated second member slidably engaged in the second lumen, wherein the second member has a portion bendable in a radially extendable bowed configuration from the retracted position to the extended position for abutment against an internal wall of a patient's cardiovascular system, the second member further having a first end embedded in the first member; and means for extending the second member, having a thumbwheel mechanism coupled to the second member, so that rotation of the thumbwheel slidably advances the second member relative to the first member second lumen and bends the second member into the bowed extended position.

The present invention also relates to a method for performing angioplasty of a constriction site in a vessel of a patient's cardiovascular system and comprises entering the cardiovascular system; pericutaneously translating through the cardiovascular system to a desired location proximate the constriction; abutting against an internal wall of the patient's cardiovascular system; and advancing towards the constriction in a direction generally opposite the abutting, for overcoming resistance by the constriction to the advancing and dilating the vessel at the constriction site.

BRIEF DESCRIPTION OF THE FIGURES

FIG. 1 is schematic cross-sectional elevation of one embodiment of a catheter of the present invention, shown in a patient's aortic root and left main coronary artery.

FIG. 2 is an elevational view of the catheter shown in FIG. 1, with the ends thereof broken away.

FIG. 3 is a cross-sectional view of the catheter shown in FIG. 2, taken along section 3—3 thereof.

FIG. 4 is a detailed plan view of the catheter embodiment shown in FIG. 2.

FIG. 5 is an elevational view of a second embodiment of a catheter of the present invention, with one end thereof broken away.

FIG. 6 is a cross-sectional view of the catheter shown in FIG. 5, taken along section 6—6 thereof.

DETAILED DESCRIPTION OF THE INVENTION

The following examples are illustrative of the angioplasty guiding catheters and methods for performing angioplasty of the present invention, but they in no way are intended to restrict the scope of the claims hereto.

The present invention includes an angioplasty guiding catheter comprising an elongated first member having at least one lumen therethrough and a tip; at least one leg member, coupled to the first member, radially extendable from a retracted position generally in contact with the first member to an extended position generally away from the first member, for abutment against an internal wall of a patient's cardiovascular system and means for extending the leg member from the retracted position to the extended position; the extending means is coupled to the leg member. The leg member may comprise a resilient, elongated second member having a portion thereof bendable in a radially extendable bowed configuration from the retracted position to the extended position, and the second member may have a first end embedded in the first member.

The catheter first member may have a second lumen and the second member is slidably engaged therein. Both the second member and the second lumen may have corresponding non-circular cross-sections, such as D-shaped cross-sections. The first member may have an outer surface having a groove thereon and the second member bendable portion is receivable in the first member groove when the bendable portion is in the collapsed position. The catheter may have at least two leg members and the means for extending the leg members may be a thumbwheel mechanism or a locking collar.

In another embodiment, the angioplasty guiding catheter comprises an elongated first member having first and second luma and a tip; at least one leg member, radially extendable from a retracted position generally in contact with the first member to an extended position generally away from the first member, having a resilient, elongated second member slidably engaged in the second lumen, the second member having a portion thereof bendable in a radially extendable bowed configuration from the retracted position to the extended position for abutment against an internal wall of a patient's cardiovascular system, the second member further having a first end embedded in the first member, and means for extending the second member, having a thumbwheel mechanism coupled to the second member, so that rotation of the thumbwheel slidably advances the second member relative to the first member second lumen and bends the second member into the bowed, extended position. In such embodiment the first member may also have an outer surface having at least two grooves thereon and at least two second luma, at least two second members, and wherein the bendable portions of each second member is receivable in a first member groove when the bendable portion is in the collapsed position.

The present invention also relates to a method for performing angioplasty of an constriction site in a vessel of a patient's cardiovascular system, comprising entering the cardiovascular system, pericutaneously translating through the cardiovascular system to a desired location proximate the constriction, abutting against an internal wall of the patient's cardiovascular system, advancing towards the constriction in a direction generally opposite the abutting, for overcoming resistance by the constriction to the advancing and dilating the vessel at the constriction site.

In this method, the abutting may be performed with a catheter having an elongated first member and at least one leg member, coupled to the first member that is radially extendable from a retracted position generally in contact with the first member to an extended position generally away from the first member by extending the leg member and contacting the internal wall therewith. The advancing may be performed by translating an angioplasty instrument through the first member lumen and positioning the instrument in the constriction, and such instruments may include a balloon dilation catheter, a guide wire, an angioscope or a laser angioplasty catheter.

In the method, the leg member may be a resilient, elongated second member having a portion thereof bendable in a radially extendable bowed configuration from the retracted position to the extended position Generally, FIG. 1 shows schematically a first blood vessel 1 and specifically, the aortic root of a patient's cardiovascular system and a second blood vessel 2 branching off the first blood vessel which is shown as the left main coronary artery, having a lesion therein, which is shown schematically as an obstruction 3. The terms constriction, obstruction and lesion are used interchangeably to describe reductions in a blood vessel's flow cross-section, that inhibits blood flow.

Referring generally to FIGS. 1 and 2, there is shown a guiding catheter 10 of the present invention having an elongated first member 11 having any desired length, diameter or molded configuration, such as those previously known in the art. If desired, the first member 11 may be constructed of a resilient plastic material and may also have a wire reinforcement (not shown) embedded therein to provide greater stiffness to the catheter. The first member 11 has a first lumen 12 therethrough for receipt of angioplasty instruments, such as balloon dilation catheters, guide wires, angioscopes and laser angioplasty catheters; the construction and use of such instruments is already known to physicians.

As shown in FIGS. 2 and 3, the first member 11 preferably has a second lumen 13 which slidably receives a resilient, elongated second member 14 with a first end 15. The second member 14 forms a extendable and bendable portion 16 by configuring the second lumen 13 to exit to the outside of the first member 11, at position 17 shown in FIG. 2, and re-enter the first member 11 at a position 18 shown in FIG. 2. The second lumen 13 exit location 17, as shown in FIG. 4, has an eye-shaped configuration, corresponding to a projection of the D-shaped configuration of the second lumen 13 and second member 14. The re-entry position 18 of the second lumen 13 has a similar configuration. Preferably the second lumen 13 and second member 14 have a non-circular cross section, such as the D-shaped cross-section shown in FIG. 3. Referring to FIG. 2, the second member first end 15 is embedded into the first member 11; the embedding may be accomplished by inserting a plug 19 into the second lumen to prevent further advancement of the second member first end 15.

As shown in FIG. 1, the bendable or bowed portion 16 acts as a leg member that is radially extendable from a retracted position generally in contact with the first member 11 to an extended position generally away from the first member for abutment against an internal wall of the patient's cardiovascular system, such as the first blood vessel inner wall 4, shown in FIG. 1. The second member 14 is desirably constructed of a resilient material, such as solid polypropylene or metal wire, which can add considerable stiffness to the guiding catheter 10 structure Referring generally to Figs. 1 and 2, slidable advancement of the second member 14 into the second lumen 13, i.e. towards the catheter tip 20, radially extends the bowed portion 16 away from the first member 11. As shown in FIG. 1, the means for extending the bowed portion 16 is a thumbwheel mechanism 21 having any construction known to those skilled in the art. Alternatively, the means for extending the bowed portion 16, may be manual advancement by the physician and the second member 14 may be locked in the advanced position by a locking collar (not shown). Radial extension of the leg member, shown as second member bowed portion 16, allows for a selected, adjustable abutment of the second member against a patient's blood vessel inner wall 4 and inhibits backing out of the catheter 10 when a balloon catheter 22 is advanced against obstruction 3. The construction of the bowed portion 16 of the present invention also allows for selective lever-like application of biasing force against obstruction 3 wherein the first member and balloon catheter act as a lever bar and the second member bowed portion 16 acts as a lever fulcrum.

FIGS. 5 and 6 show another embodiment of a guiding catheter 23 of the present invention having a pair of leg members or second members 24 which allow more secure abutment against a blood vessel wall in bipod-like fashion The guiding catheter 23 may be constructed with two or more second members 24 and the radial extension of the bowed portions 25 may be independently controlled by means for advancing the second members 24 (not shown). The first member 26 embodiment shown in FIGS. 5 and 6 has grooves 27 constructed in the outer surface thereof for receipt of the bendable portions 25 of each second member, when the bendable portions are in the collapsed position, i.e. the second member 24 is retracted away from first member tip 28. Similarly, the first member embodiment 11, shown in FIG. 2 may also be constructed with such grooves.

The present invention method for performing angioplasty is shown in FIG. 1, and is performed by entering the cardiovascular system, such as by an incision in the femoral artery, pericutaneously translating through the cardiovascular system vessels to a desired location proximate the lesion or obstruction 3 as shown in FIG. 1; abutting against an internal wall 4 of the cardiovascular system, such as by extending the leg member, which in FIG. 1 is the second member 14 bendable bowed portion 16. The next step in the present invention is advancing the balloon catheter 22 out of the guiding catheter 10 and towards the constriction 3 in a direction generally opposite the abutting. In FIG. 1, the abutting by catheter 10 occurs from right to left and the advancing occurs generally from left to right toward the obstruction 3. After advancing of the balloon catheter 13 completed, it is inflated by techniques known to physicians, which dilates the second blood vessel 2 at the obstruction 3.

What is claimed is:

1. An angioplasty guiding catheter comprising:
   an elongated first member having at least one lumen therethrough and a tip;
   at least one leg member, coupled to the first member, radially extendable from a retracted position generally in contact with the first member to an extended position generally away from the first member, for abutment against an internal wall of a patient's cardiovascular system; and
   means for extending the leg member from the retracted position to the extended position, the extending means being coupled to the leg member.

2. The catheter of claim 1, wherein the leg member comprises a resilient, elongated second member having a portion thereof bendable in a radially extendable bowed configuration from the retracted position to the extended position.

3. The catheter of claim 2, wherein the second member has a first end embedded in the first member.

4. The catheter of claim 2, wherein the first member has a second lumen and the second member is slidably engaged therein.

5. The catheter of claim 4, wherein the second member and the second lumen have a corresponding non-circular cross-section 6. The catheter of claim 4, wherein the second member and the second lumen have a corresponding D-shaped cross-section.

7. The catheter of claim 2, wherein the first member has a second lumen and an outer surface having a groove thereon, the second member is slidably engaged in the second lumen and the second member bendable portion is receivable in the first member groove when the bendable portion is in the collapsed position.

8. The catheter of claim 2, having at least two leg members.

9. The catheter of claim 2, wherein the means for extending the leg member is a thumbwheel mechanism.

10. The catheter of claim 2, wherein the means for extending the leg member is a locking collar.

11. An angioplasty guiding catheter comprising:
    an elongated first member having first and second luma and a tip;
    at least one leg member, radially extendable from a retracted position generally in contact with the first member to an extended position generally away from the first member, having a resilient, elongated second member slidably engaged in the second lumen, the second member having a portion thereof bendable in a radially extendable bowed configuration from the retracted position to the extended position for abutment against an internal wall of a patient's cardiovascular system the second member further having a first end embedded in the first member; and
    means for extending the second member, having a thumbwheel mechanism coupled to the second member, so that rotation of the thumbwheel slidably advances the second member relative to the first member second lumen and bends the second member into the bowed, extended position.

12. The catheter of claim 11, wherein the first member has an outer surface having at least two grooves thereon and at least two second luma; at least two second members, and wherein the bendable portions of each second member is receivable in a first member groove when the bendable portion of each is in the collapsed position.

13. In a patient, a method for performing angioplasty of a constriction site in a vessel of the patient's cardiovascular system comprising:
   entering the cardiovasular system;
   pericutaneously translating through the cardiovascular system to a desired location proximate the constriction;
   abutting against an internal wall of the patient's cardiovascular system;
   advancing towards the constriction in a direction generally opposite the abutting, for overcoming resistance by the constriction to the advancing; and
   dilating the vessel at the constriction.

14. The method of claim 13, wherein the abutting is performed with a catheter having an elongated first member and at least one leg member coupled to the first member that is radially extendable from a retracted position generally in contact with the first member to an extendable position generally away from the first member by extending the leg member and contacting the internal wall therewith 15. The method of claim 14, wherein the advancing is performed by translating an angioplasty instrument through the first member lumen and positioning the instrument in the constriction.

16. The method of claim 15, wherein the instrument includes a balloon dilation catheter.

17. The method of claim 15, wherein the instrument includes a guide wire.

18. The method of claim 15, wherein the instrument includes an angioscope.

19. The method of claim 15, wherein the instrument includes a laser angioplasty catheter.

20. The method of claim 14, wherein the leg member is a resilient, elongated second member having a portion thereof bendable in a radially extendable bowed configuration from the retracted position to the extended position.

* * * * *